(12) United States Patent
Riedl

(10) Patent No.: US 6,743,416 B2
(45) Date of Patent: Jun. 1, 2004

(54) SUNSCREEN FOR ANIMALS

(76) Inventor: Bonnie Riedl, 2902 Whitetail Rd., Gold Canyon, AR (US) 85218

( * ) Notice: Subject to any disclaimer, the term of this patent is extended or adjusted under 35 U.S.C. 154(b) by 0 days.

(21) Appl. No.: 10/262,475

(22) Filed: Sep. 30, 2002

(65) Prior Publication Data

US 2004/0062725 A1 Apr. 1, 2004

(51) Int. Cl.$^7$ ................................... A61K 7/42
(52) U.S. Cl. ................ 424/59; 424/400; 424/401; 424/642
(58) Field of Search ............... 424/59, 69, 400, 424/401, 642

(56) References Cited

U.S. PATENT DOCUMENTS

| | | |
|---|---|---|
| 1,818,699 A | 8/1931 | Dusenbury et al. |
| 2,826,169 A | 3/1958 | Le Veen |
| 5,032,390 A | 7/1991 | Iwaya et al. ................ 424/59 |
| 5,298,065 A | 3/1994 | Hiraoka et al. ............ 106/425 |
| 5,340,567 A | 8/1994 | Cole et al. ................... 424/59 |
| 5,424,055 A | 6/1995 | Hayashi et al. ............ 423/622 |
| 5,709,847 A | 1/1998 | Bissett et al. .............. 424/59 |
| 2002/0041853 A1 | 4/2002 | Ishii et al. |

OTHER PUBLICATIONS

Milks Practical Veterinary Pharmacology, p. 523.*

* cited by examiner

Primary Examiner—Neil S. Levy
(74) Attorney, Agent, or Firm—The Halvorson Law Firm

(57) ABSTRACT

Disclosed are sunscreen compositions comprising a combination of titanium dioxide and zinc oxide being present in a weight ratio of from about 10:1 to 1:10 and the total of said titanium dioxide and zinc oxide comprises greater than 60% by weight of the total composition. Also disclosed is a method for reducing sunburn on animals comprising the step of topically apply a composition comprising a combination of titanium dioxide and zinc oxide being present in a weight ratio of from about 10:1 to 1:10 and the total of said titanium dioxide and zinc oxide comprises greater than 60% by weight of the total composition onto exposed skin of the animal.

2 Claims, No Drawings

SUNSCREEN FOR ANIMALS

FIELD OF THE INVENTION

The present invention relates to sun blocking preparations and methods therefor, for application on the skin of animals. More specifically, the present invention relates to a substantially inorganic preparation for the application on the skin of animals.

BACKGROUND

Sun blocking formulations, typically known as sunscreens, are prepared from a variety of materials. All sunscreens, to date, have been made from a combination of organic and inorganic compounds. The organic compounds are primarily transport and skin treatment media for the inorganic compounds, but may include ultraviolet absorbing organic compounds. The primary inorganic compound used in sunscreens is titanium dioxide in its most common form rutile.

Because sunscreens are primarily used on humans, these are formulated to be clear or nearly invisible. In order to accomplish this goal, the concentration of the inorganic portion necessarily must be low.

Because of the low concentration of inorganic materials, and high concentration or water soluble, or partially water soluble, organic compounds, these sunscreens require frequent reapplication. Moreover, these formulation are designed to let varying portions of the ultraviolet light through in order to allow the wearer to gains an cosmetically acceptable "tan".

Thus, it is obvious that there is a need for a sunscreen that does not require frequent reapplication and has a greatly reduced water solubility.

SUMMARY OF INVENTION

It is an object of the present invention to provide an inorganic sunscreen that is long lasting and, therefore, requires fewer application.

It is another object of the present invention to provide a sunscreen that comprises a combination of titanium dioxide and zinc oxide being present in a weight ratio of from about 10:1 to 1:10 and the total of said titanium dioxide and zinc oxide comprises greater than 60% by weight of the total composition.

It is a further object of the present invention to provide a composition as above wherein the total of said titanium dioxide and zinc oxide comprises greater than 75% by weight of the total composition.

It is yet another object of the present invention to provide a composition as above wherein the total of said titanium dioxide and zinc oxide comprises greater than 90% by weight of the total composition.

It is still yet another object of the present invention to provide a composition as above wherein the total of said titanium dioxide and zinc oxide comprises 100% by weight of the total composition.

It is yet a further object of the present invention to provide a composition as above wherein the weight ratio ranges from about 5:1 to 1:5.

It is still yet a further object of the present invention to provide a composition as above wherein the weight ratio ranges from about 2:1 to 1:2.

It is another object of the present invention to provide a composition as above wherein the weight ratio ranges from about 1:1 to 1:1.

The novel features that are considered characteristic of the invention are set forth with particularity in the appended claims. The invention itself, however, both as to its structure and its operation together with the additional object and advantages thereof will best be understood from the following description of the preferred embodiment of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

The formulation according to the present invention is useful as a sun blocking preparation. Furthermore, the formulation according to the present invention is particularly useful as a sun blocking preparation for non-human animals.

The present invention is a formulation that comprises primarily inorganic metal oxides. More specifically, in the preferred embodiment, the metal oxides are both titanium dioxide and zinc oxide.

In its most preferred form, the formulation according to the present invention is comprised of only these two metal oxides. Lesser preferred embodiments include other inorganic oxides, but are considered to fall within the scope of the present invention.

These two metal oxides, according to the present invention, comprise greater than 60%, by weight, of the sun blocking formulation, with the most preferred embodiment comprising greater than 95% by weight of the sun blocking formulation.

The ratio between these two preferred metal oxides may vary, but are preferred to range between 10:1 and 1:10 titanium dioxide:zinc oxide. The most preferred ratio, however is 1:1.

It is preferred that the composition according to the present invention contain no organic materials, such as those typically used as transport media in sunscreens. This lack of organic transport material leaves the composition a dry powder that is easily topologically applied to the surface of the skin of an animal. It is felt that the dry nature of the preferred embodiment is important since different chemicals affect different animal skins in different ways. That is, a chemical that acts as a soothing emollient for human skin may be an irritant to certain exposed skin on a horse or cow. The composition according to the present invention, because of the inorganic nature of the oxides that form the primary components, are inherently biocompatible and should not irritate different animal skins.

In use, the composition may be manually applied, such as by hand or with a pad, or may be mechanically applied, such as by a powder spray or the like. When applied, the applicator may be either damp or dry, as the application situation requires.

In an alternate embodiment, the composition may be dispersed in a highly volatile liquid and applied by atomization (spraying) onto the surface of the skin. The highly volatile liquid then evaporates, thereby leaving the composition according to the present invention to protect the surface of the skin.

The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for reducing sunburn on animals comprising the step of topically applying a composition consisting of a combination of titanium dioxide and zinc oxide being present in a weight ratio of 1:1 and the total of said titanium dioxide and zinc oxide is 100% by weight of the total composition onto exposed animal.

2. A method for reducing sunburn on animals comprising the step of topically applying a composition consisting essential of a combination of titanium dioxide and zinc oxide being present in a weight ratio of from about 2:1 to 1:2 and the total of said titanium dioxide and zinc oxide comprises greater than 90% by weight of the total composition onto exposed skin of the animal.

* * * * *